(12) United States Patent
Wollenberg et al.

(10) Patent No.: US 7,069,203 B2
(45) Date of Patent: Jun. 27, 2006

(54) METHOD AND SYSTEM OF PRODUCT DEVELOPMENT PROCESS FOR CHEMICAL COMPOSITIONS USING HIGH VOLUME MODELING

(75) Inventors: Robert H. Wollenberg, Orinda, CA (US); Thomas J. Balk, San Francisco, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 336 days.

(21) Appl. No.: 10/699,506

(22) Filed: Oct. 31, 2003

(65) Prior Publication Data

US 2005/0096895 A1 May 5, 2005

(51) Int. Cl.
*G06G 7/48* (2006.01)

(52) U.S. Cl. .............. 703/9; 703/2; 705/10; 436/60
(58) Field of Classification Search ............ 703/9, 703/2
See application file for complete search history.

(56) References Cited

U.S. PATENT DOCUMENTS

| | | |
|---|---|---|
| 5,959,297 A | 9/1999 | Weinberg et al. |
| 5,985,356 A | 11/1999 | Shultz et al. |
| 6,004,617 A | 12/1999 | Shultz et al. |
| 6,030,917 A | 2/2000 | Weinberg et al. |
| 6,034,775 A | 3/2000 | McFarland et al. |
| 6,045,671 A | 4/2000 | Wu et al. |
| 6,087,181 A | 7/2000 | Cong |
| 6,149,882 A | 11/2000 | Guan et al. |
| 6,157,449 A | 12/2000 | Hajduk |
| 6,175,409 B1 | 1/2001 | Nielsen et al. |
| 6,182,499 B1 | 2/2001 | McFarland et al. |
| 6,187,164 B1 | 2/2001 | Warren et al. |
| 6,248,540 B1 | 6/2001 | Weinberg et al. |

(Continued)

FOREIGN PATENT DOCUMENTS

WO    WO 02/07870    1/2002

OTHER PUBLICATIONS

Waszkowycz et al., B. Large-Scale Virtual Screening for Discovering Leads in the Postgenomic Era, IBM-Systems-Journal, vol. 40, No. 2, pp. 360-376, 2001.*

(Continued)

*Primary Examiner*—Russell Frejd
(74) *Attorney, Agent, or Firm*—Claude J. Caroli; M. Carmen & Associates, PLLC

(57) ABSTRACT

A method and system of transforming a product development process to reduce time in bringing a product to market through high throughput experimentation and advanced statistics and informatics, to transform the product development to a level of higher correlation with engine tests, and to develop better commercial products. This is achieved by modeling in Silico a plurality of component molecular models; deriving in Silico molecular characteristics (descriptors) for each of the plurality of compiled molecular models; creating at least one combinatorial library database record for each of the formulations, the at least one record having a plurality of fields for storing information about compositional characteristics; receiving specification requirements for a lubricating oil composition; selecting from a database entries corresponding to compositions having specifications comparable to the received specification requirements; formulating a new lubricating oil composition to comply with received specification requirements; testing the new lubricant oil for compliance with received specification requirements; repeating the selecting, formulating, and testing steps until compliance with received specification requirements is achieved; and correlating the new lubricating oil composition to actual engine performance.

11 Claims, 5 Drawing Sheets

U.S. PATENT DOCUMENTS

| | | |
|---|---|---|
| 6,260,407 B1 | 7/2001 | Petro et al. |
| 6,265,226 B1 | 7/2001 | Petro et al. |
| 6,296,771 B1 | 10/2001 | Miroslav |
| 6,326,090 B1 | 12/2001 | Shultz et al. |
| 6,336,353 B1 | 1/2002 | Matsiev et al. |
| 6,345,528 B1 | 2/2002 | Petro et al. |
| 6,346,290 B1 | 2/2002 | Schultz et al. |
| 6,371,640 B1 | 4/2002 | Hajduk et al. |
| 6,373,570 B1 | 4/2002 | McFarland et al. |
| 6,393,895 B1 | 5/2002 | Matsiev et al. |
| 6,393,898 B1 | 5/2002 | Hajduk et al. |
| 6,395,552 B1 | 5/2002 | Borade et al. |
| 6,401,519 B1 | 6/2002 | McFarland et al. |
| 6,406,632 B1 | 6/2002 | Safir et al. |
| 6,410,331 B1 | 6/2002 | Schultz et al. |
| 6,419,881 B1 | 7/2002 | Weinberg et al. |
| 6,420,179 B1 | 7/2002 | Schultz et al. |
| 6,436,292 B1 | 8/2002 | Petro |
| 6,438,497 B1 | 8/2002 | Mansky et al. |
| 6,440,745 B1 | 8/2002 | Weinberg et al. |
| 6,441,901 B1 | 8/2002 | McFarland et al. |
| 6,461,515 B1 | 10/2002 | Safir et al. |
| 6,468,806 B1 | 10/2002 | McFarland et al. |
| 6,475,391 B1 | 11/2002 | Safir et al. |
| 6,484,567 B1 | 11/2002 | Hajduk et al. |
| 6,491,816 B1 | 12/2002 | Petro |
| 6,508,984 B1 | 1/2003 | Turner et al. |
| 6,519,032 B1 | 2/2003 | Kuebler et al. |
| 6,528,026 B1 | 3/2003 | Hajduk et al. |
| 6,535,284 B1 | 3/2003 | Hajduk et al. |
| 6,535,824 B1 | 3/2003 | Mansky et al. |
| 6,536,944 B1 | 3/2003 | Archibald et al. |
| 6,541,271 B1 | 4/2003 | McFarland et al. |
| 6,553,318 B1 | 4/2003 | Mansky |
| 6,576,906 B1 | 6/2003 | Archibald et al. |
| 6,577,392 B1 | 6/2003 | Nielsen et al. |
| 6,582,116 B1 | 6/2003 | Nielsen |
| 6,605,473 B1 | 8/2003 | Hajduk et al. |
| 6,644,101 B1 | 11/2003 | Hajduk et al. |
| 6,649,413 B1 | 11/2003 | Schultz et al. |
| 6,650,102 B1 | 11/2003 | Hajduk et al. |
| 6,653,138 B1 | 11/2003 | Turner et al. |
| 6,655,194 B1 | 12/2003 | Hajduk et al. |
| 6,658,429 B1 | 12/2003 | Dorsett, Jr. |
| 6,664,067 B1 | 12/2003 | Hajduk et al. |
| 6,668,622 B1 | 12/2003 | Hajduk et al. |
| 6,670,298 B1 | 12/2003 | Weinberg et al. |
| 6,679,130 B1 | 1/2004 | Hajduk et al. |
| 6,681,618 B1 | 1/2004 | Hajduk et al. |
| 6,686,205 B1 | 2/2004 | Shultz et al. |
| 6,690,179 B1 | 2/2004 | Hajduk et al. |
| 2002/0023507 A1 | 2/2002 | Hajduk et al. |
| 2002/0028456 A1 | 3/2002 | Manksy et al. |
| 2002/0029621 A1 | 3/2002 | Hajduk et al. |
| 2002/0032531 A1 | 3/2002 | Mansky et al. |
| 2002/0098332 A1 | 7/2002 | Warren et al. |
| 2002/0148282 A1 | 10/2002 | Hajduk et al. |
| 2002/0155036 A1 | 10/2002 | Hajduk et al. |
| 2002/0164275 A1 | 11/2002 | Wheeler et al. |
| 2003/0007152 A1 | 1/2003 | McFarland et al. |
| 2003/0032198 A1 | 2/2003 | Lugmair et al. |
| 2003/0032205 A1 | 2/2003 | McFarland et al. |
| 2003/0037601 A1 | 2/2003 | Mansky et al. |
| 2003/0037620 A1 | 2/2003 | Mansky |
| 2003/0041653 A1 | 3/2003 | Matsiev et al. |
| 2003/0041671 A1 | 3/2003 | Hajduk et al. |
| 2003/0041672 A1 | 3/2003 | Hajduk et al. |
| 2003/0041676 A1 | 3/2003 | Hajduk et al. |
| 2003/0054740 A1 | 3/2003 | Mansky |
| 2003/0055587 A1 | 3/2003 | Wang et al. |
| 2003/0056576 A1 | 3/2003 | Mansky |
| 2003/0068829 A1 | 4/2003 | Giaquinta et al. |
| 2003/0097871 A1 | 5/2003 | Mansky |
| 2003/0100119 A1 | 5/2003 | Weinberg et al. |
| 2003/0127776 A1 | 7/2003 | Carlson et al. |
| 2003/0133113 A1 | 7/2003 | Hajduk et al. |
| 2003/0138025 A1 | 7/2003 | Archibald et al. |
| 2003/0141613 A1 | 7/2003 | Hajduk et al. |
| 2003/0142309 A1 | 7/2003 | Kuebler et al. |
| 2003/0157721 A1 | 8/2003 | Turner et al. |
| 2003/0161763 A1 | 8/2003 | Erden et al. |
| 2003/0169638 A1 | 9/2003 | Nielsen |
| 2003/0190260 A1 | 10/2003 | Wheeler et al. |
| 2003/0203500 A1 | 10/2003 | Carlson et al. |
| 2003/0211016 A1 | 11/2003 | Dales et al. |
| 2003/0218467 A1 | 11/2003 | Carlson et al. |
| 2003/0219906 A1 | 11/2003 | Giaquinta et al. |
| 2004/0123650 A1 | 7/2004 | Kolosov et al. |
| 2005/0092072 A1* | 5/2005 | Wollenberg et al. ........ 73/53.05 |
| 2005/0095714 A1* | 5/2005 | Wollenberg et al. .......... 436/55 |
| 2005/0095716 A1* | 5/2005 | Wollenberg et al. .......... 436/60 |
| 2005/0095717 A1* | 5/2005 | Wollenberg et al. .......... 436/60 |
| 2005/0095718 A1* | 5/2005 | Wollenberg et al. .......... 436/60 |

OTHER PUBLICATIONS

Wildberger, A.M. Complex Adaptive Systems: Concepts and Power Industry Applications, IEEE, Control Systems Magazine, vol. 17, No. 6, Dec. 1997, pp. 77-88.*

* cited by examiner

METHOD AND SYSTEM OF PRODUCT DEVELOPMENT PROCESS FOR CHEMICAL COMPOSITIONS USING HIGH VOLUME MODELING

BACKGROUND OF THE INVENTION

1. Technical Field

The present invention relates generally to a method and system of product development process for chemical compositions using high volume modeling.

2. Description of the Related Art

The use of a combinatorial approach for materials synthesis is a relatively new area of research aimed at using rapid synthesis and screening methods to build libraries of polymeric, inorganic or solid state materials. For example, advances in reactor technology have empowered chemists and engineers to rapidly produce large libraries of discrete organic molecules in the pursuit of new drug discovery, which have led to the development of a growing branch of research called combinatorial chemistry. Combinatorial chemistry generally refers to methods and materials for creating collections of diverse materials or compounds—commonly known as libraries—and to techniques and instruments for evaluating or screening libraries for desirable properties.

Presently, research in the lubricant industry involves individually forming candidate lubricating oil compositions and then performing a macro-scale analysis of the candidate compositions by employing a large amount of the candidate to be tested. Additionally, the methods employed for testing each candidate composition require manual operation. This, in turn, significantly reduces the number of compositions that can be tested and identified as leading lubricating oil compositions.

Drawbacks associated with conventional screening procedures can be seen as follows. For example, governmental and automotive industry pressure towards reducing the phosphorous and sulfur content of lubricating oil compositions is leading to new research to identify oil compositions which can satisfy certain tests such as, for example, oxidation, wear and compatibility tests, while containing low levels of phosphorous and sulfur. For instance, United States Military Standards MIL-L-46152E and the ILSAC Standards defined by the Japanese and United States Automobile Industry Association at present require the phosphorous content of engine oils to be at or below 0.10 wt. % with future phosphorous content being proposed to even lower levels, e.g., 0.08 wt. % by January, 2004 and below 0.05 wt. % by January, 2006. Also, at present, there is no industry standard requirement for sulfur content in engine oils, but it has been proposed that the sulfur content be below 0.2 wt. % by January, 2006. Thus, it would be desirable to decrease the amount of phosphorous and sulfur in lubricating oils still further, thereby meeting future industry standard proposed phosphorous and sulfur contents in the engine oil while still retaining the oxidation or corrosion inhibiting properties and antiwear properties of the higher phosphorous and sulfur content engine oils.

Typically, once a group of lubricating oil compositions selected to address a certain requirement, for example the amount of phosphorous and sulfur, has been prepared, no additional tests related to numerous properties of the oil compositions of the selected group, are performed. As a consequence, oftentimes testing additional properties of the selected group of oil compositions, which include, for example, the properties tested during a variety of wear tests, comes as an afterthought. Yet, ensuring proper antiwear properties of lubricating oil compositions are critical to successful operation and maintenance of mechanical systems, such as automobile engines. Laboratory lubricant analysis is time consuming and costly. Furthermore, the laboratories are typically not sufficiently automated, which leads to performing the same lengthy procedure every time a new lubricating oil composition is being tested.

Thus, present research in the lubricant industry does not allow for diverse and rapid testing of lubricating oil compositions. As such, there exists a need in the art for a more efficient, economical and systematic approach for the bench testing of lubricating oil compositions and screening of such compositions for information potentially bearing upon the actual useful properties of the compositions.

Accordingly, it would be desirable to rapidly screen a plurality of sample candidate lubricating oil compositions utilizing small amounts to automatically determine and catalog the desired lubricating properties. In this manner, a method and system of product development process for chemical compositions using high volume modeling can be achieved.

SUMMARY OF THE INVENTION

The key variables with regard to the efficacy of modeling approaches are the relative complexity of the basic product from a molecular point of view and the number of variations from the basic product, e.g., formulations. Lubricating oil additives are characterized by relatively complex products and numerous variations and formulations of the basic components. In addition, throughout the product development chain, lubricating oil additives are characterized by a series of often relatively poor correlating tests, but with the ultimate testing platform, e.g., engine tests, being very expensive. In such a complex, noisy test environment, molecular-level modeling will be the least effective approach, although it may facilitate innovation with regard to radically different chemistries. Advanced, comprehensive statistical inferencing is guaranteed to be critical in this environment, but limited by the number of physical test points and inherent noise. High throughput experimentation (HTE) seems particularly well suited to lubricating oil additives or lubricating oil compositions containing such additives, as in combination with statistical inferencing, it can generate the large number of physical tests required to increase the depth and breadth of the product "formulation landscape". HTE and associated advanced statistical inferencing is ideally suited for lubricating oil additives and formulated lubricating oil compositions.

The present invention is guided by making improvements in the ability to make confident inferences from test results and the volume of tests on formulation variations that can be conducted. In the molecular modeling step there is an opportunity, through enhanced processes, to achieve benefits with regard to improving test inferencing confidence. In the comprehensive statistical inferencing step, this can be supplemented by application of quantitative structure activity relationship (QSAR) techniques. In the HTE step, basic HTE is applied, with bench tests at current correlation levels miniaturized and included within the HTE infrastructure. In the bench test step, miniaturized tests with better correlation than existing bench tests will be integrated into the HTE infrastructure.

The present invention describes a method and system of transforming a product development process to reduce time to bring a product to market through high throughput experimentation and advanced statistics and informatics. The present invention transforms the product development process to a level of higher correlation with engine tests, and to develop better commercial products. This is achieved by in Silico modeling of a plurality of component molecular models using quantum mechanical (QM) software method; in Silico deriving molecular characteristics (descriptors) for each of the plurality of compiled molecular models performed by QSAR software. As used herein, the expression "in Silico" or "in Silico modeling" refers to a computational work.

The present invention further includes at least creating at least one combinatorial library database record for each of the formulations, and at least one record having a plurality of fields for storing information about compositional characteristics. The libraries include component combinations and an entire mixture of lubricating oil additives or lubricating oil compositions containing at least one base oil of lubricating viscosity and at least one lubricating oil additive. The formation and management is performed by a software program managing a relational database, such as, e.g., Oracle.

New lubricating oil compositions are requested by receiving specification requirements. These lubricating oil compositions are formed by selecting from the database entries corresponding to compositions having specifications comparable to the received specification requirements, formulating a new lubricating oil composition to comply with received specification requirements, and testing the new lubricating oil composition for compliance with received specification requirements. The formation steps are repeated until full compliance with received specification requirements is achieved; and correlating the composition to actual engine performance.

BRIEF DESCRIPTION OF THE DRAWINGS

The foregoing and other objects, aspects, and advantages of the present invention will be better understood from the following detailed description of preferred embodiments of the invention with reference to the accompanying drawings that include the following.

DETAILED DESCRIPTION OF THE PREFERRED EMBODIMENT(S)

Figure 1A:
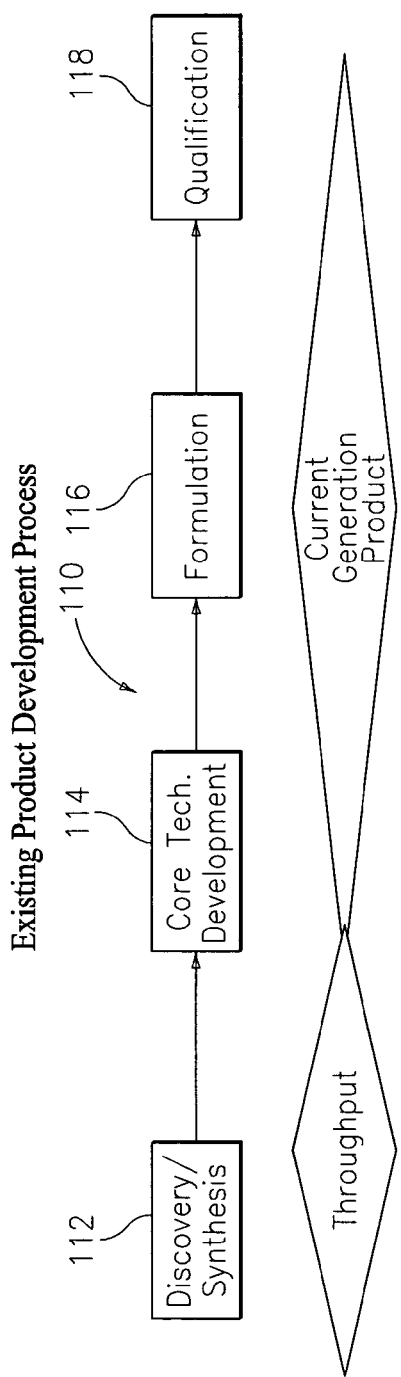
FIG. 1a is a block diagram of a method of formulating lubricating oil compositions of the prior art.
Figure 1B:
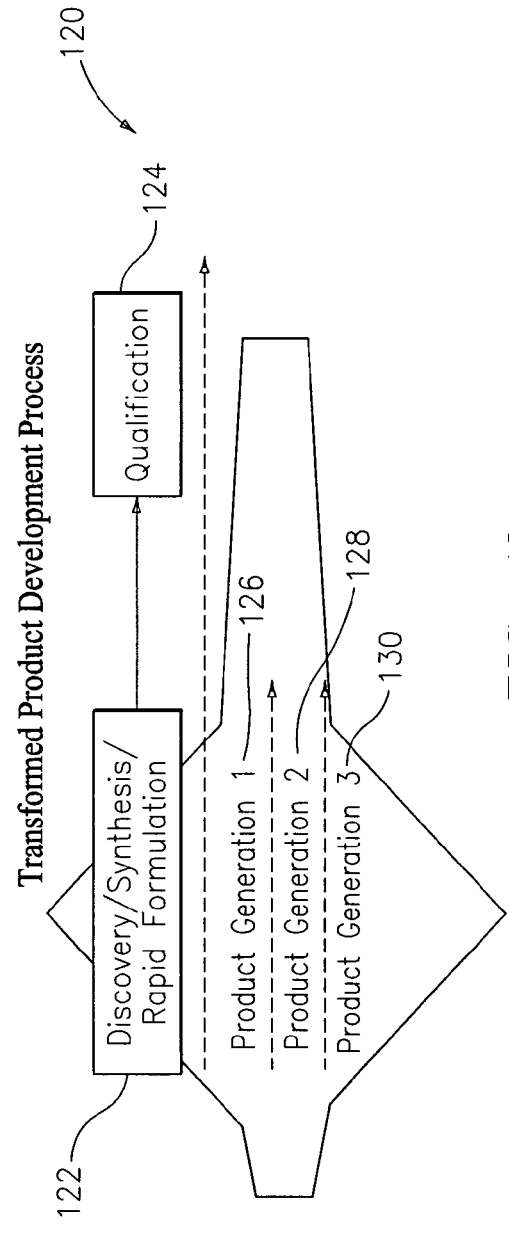
FIG. 1b is a block diagram of a method of formulating lubricating oil compositions of the present invention.

FIGS. 1a and 1b illustrate a comparison of the existing technology process flow 110 from the discovery/synthesis step 112 to the core technology development step 114, through the formulation step 116 to the qualification of products step 118 (FIG. 1a), with the inventive transformed technology and associated program logic control (PLC) process 120 (FIG. 1b). The goal of the process 120 of the present invention is to rapidly formulate and test orders of magnitude more product variations. This will enable multiple generation products with different chemistries to be developed in parallel.

The purpose of the process 120 of the present invention is still the same as that of the current technology process, namely to create molecules and formulations that correlate with real engine performance called qualification. The inventive method substantially reduces the time to get from the discovery step 122 to the qualification step 124 because portions of research 126, 128, 130 will run in parallel. That is, chemists will synthesize and subsequently evaluate materials in parallel with formulator bench testing. In this way, much of the data generated by the chemists is directly applicable to the new specifications. This is quite different from the existing process 110, where a different set of formulations and bench test for testing newly made components is compared to those tests being run by formulators. Thus, because there is more efficiency, the time to market has contracted and the probability of success increased, component/product and aligned strategies are standardized. As an outcome, the strategic relationships with customers are strengthened.

Figure 2:
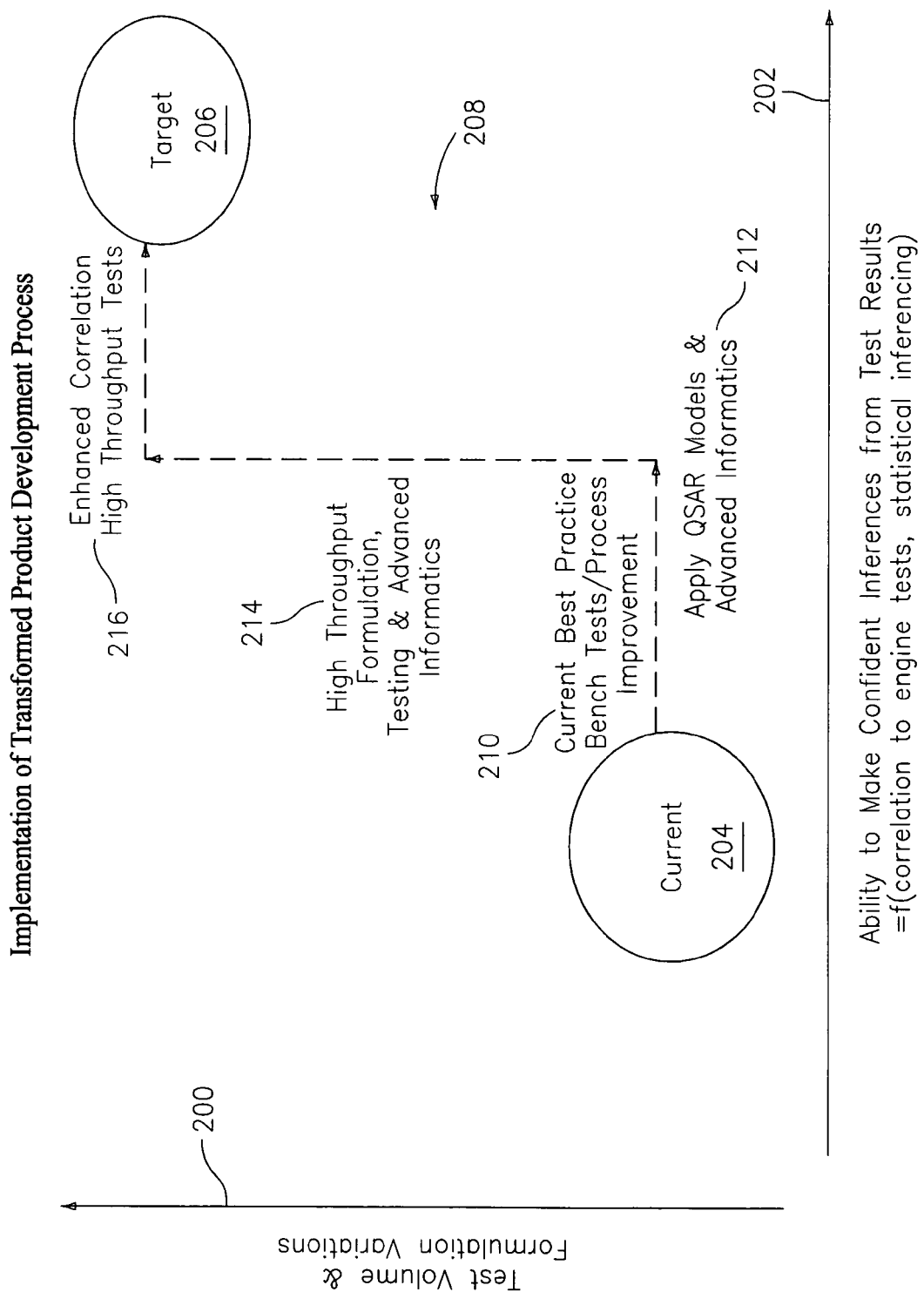
FIG. 2 is a graph of an implementation of transformed product development process showing transition to improved testing throughput of the present invention.

FIG. 2 illustrates a graph of implementation of the transformed product development process 208 plotted on an axis of a "test volume and formulation variations" 200 and an "ability to make confident inferences from test results" 202. The ability to make confident inferences from test results is a function of correlation to engine tests and statistical inferencing. Both improved testing throughput and test correlation/test inferencing must be addressed to achieve maximum results. This will require an integrated software and hardware approach. From the standpoint of cost, there is usually a preference for software solutions versus hardware solutions. It is usually less expensive to simulate with software than to develop and operate hardware solutions. However, these economics must be balanced by relative efficacy of the approaches.

To improve from a current 204 position on a graph 208 to a target 206 position, the present invention proposes performing the steps of improving a current best practice bench tests/process at step 210, apply quantitative structure activity relationship (QSAR) models and advanced informatics at step 212, perform high throughput formulation, testing and advanced informatics at step 214, and perform enhanced correlation high throughput tests at step 216.

Figure 3:
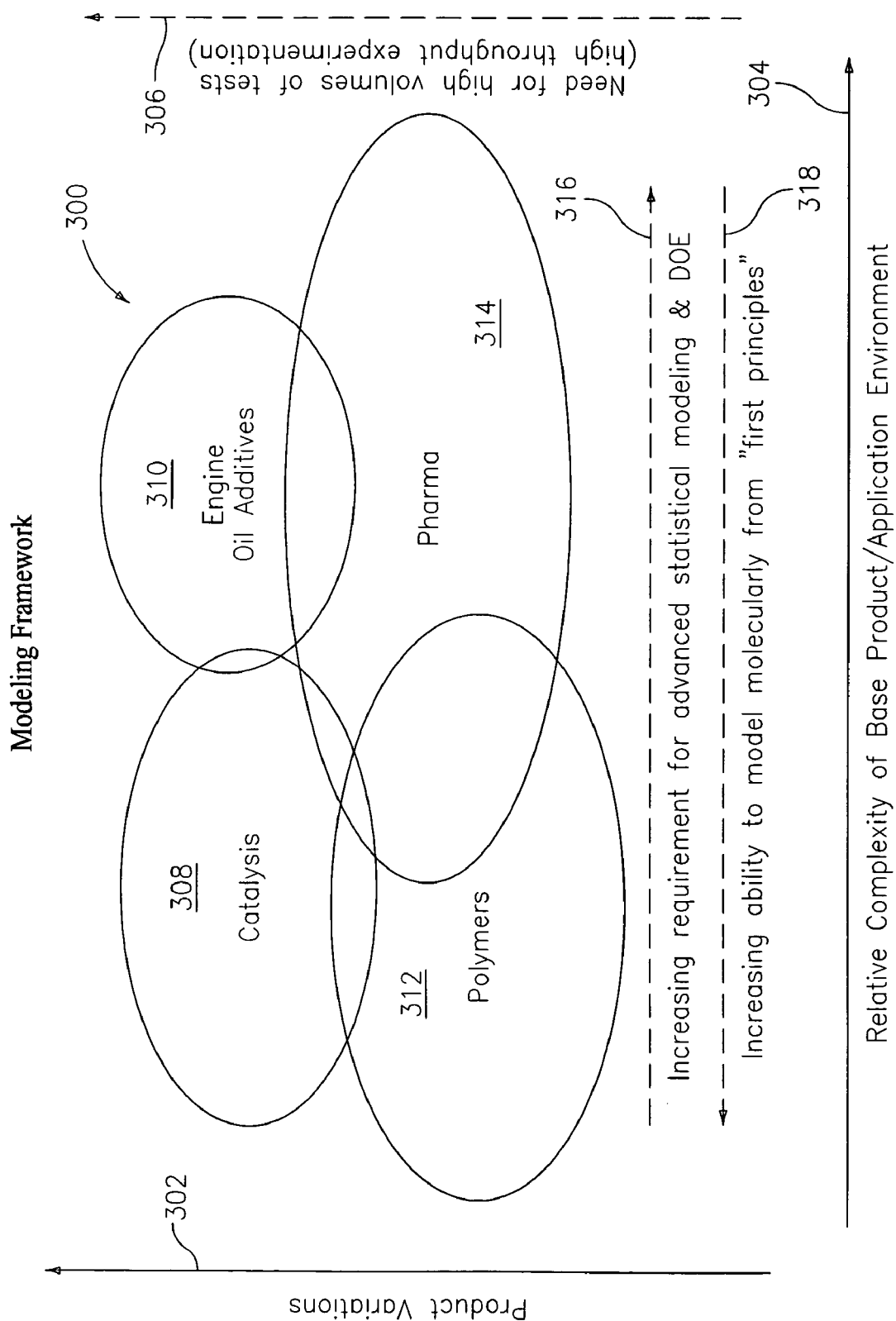
FIG. 3 is a graph of a product development modeling framework showing the need for high product variations and high complexity and product and application environment of engine oil additives.

FIG. 3 illustrates a graph of product development modeling framework 300 plotted on an axis of "product variations" 302 and "relative complexity of a base product or application environment" 304. The graph 300 shows a need for high volumes of tests or high throughput experimentation (HTE) 306 increasing along the product variations axis 302, with catalysis 308 and engine oil additives 310 requiring higher volume of tests than polymers 312 and pharma products 314.

It can also be seen from the graph 300 that as the relative complexity of a base product or application environment 304 increases so do requirement for advanced statistical modeling and design of experiments (DOE) 316. In other words, the engine oil additives 310 and pharma products 314 have a higher requirement for statistical modeling and DOE 316 than do the catalysis 308 and polymers 312.

Conversely, the ability to model molecularly from "first principles" 318 decreases in proportion to the complexity of a base product or application environment 304 and that the catalysis 308 and polymers 312 are better suited for molecular modeling from "first principles" 318 than the engine oil additives 310 and pharma products 314. Lubricating oil additives or lubricating oil compositions 310 product development transformation requires both enhanced statistical modeling/DOE approaches and HTE. Over time, integration of molecular modeling enhances the product's value even more.

Figure 4:
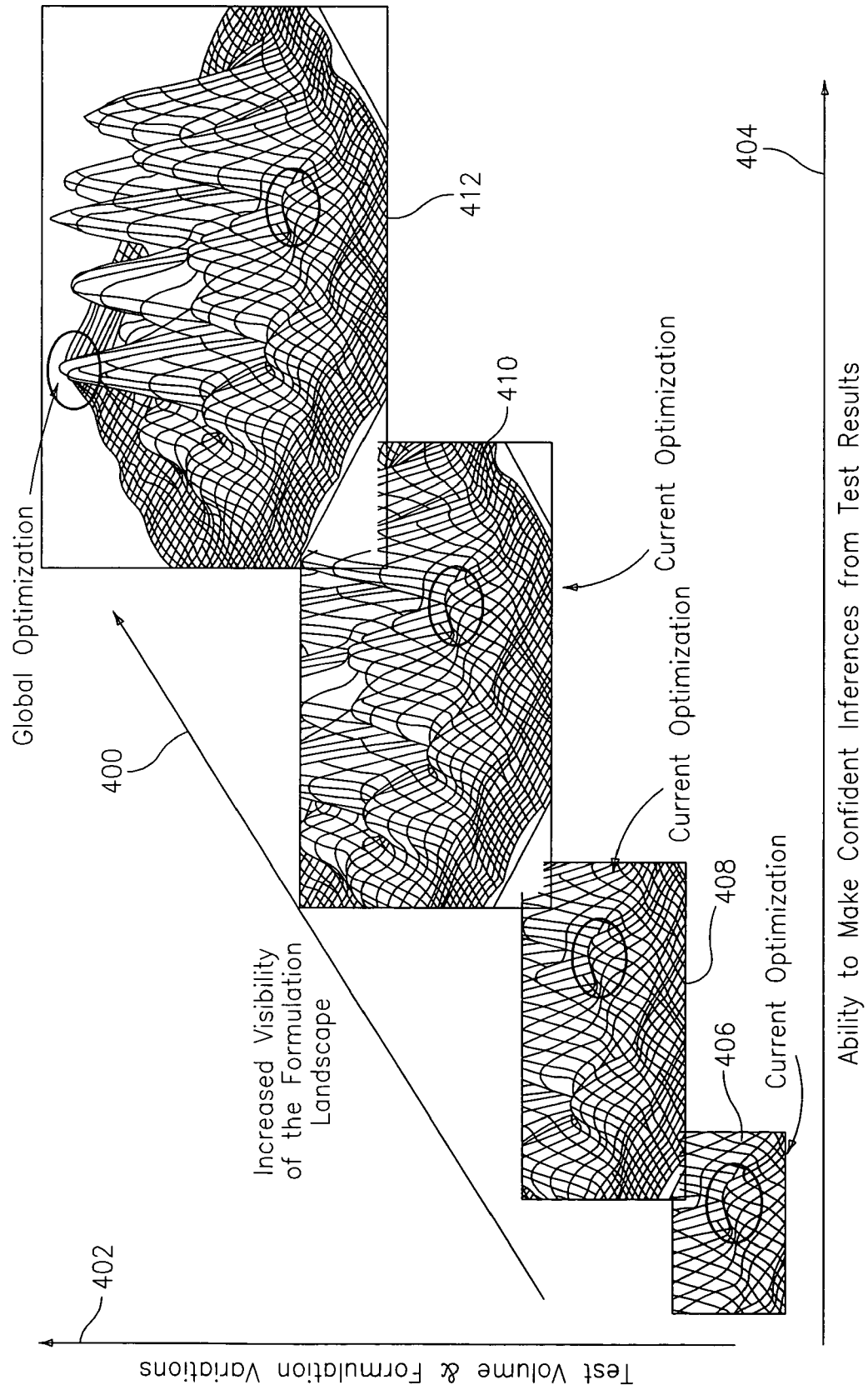
FIG. 4 is a graph of a formulation landscape and its improvement with increase in test volume and formulation variations and the ability to make confident inferences from test results; and, FIG. 5 is a block diagram of the novel product development process for lubricating oil composition of the present inventive invention.

FIG. 4 shows a graph of "increased visibility of the formulation landscape" 400. Improving the visibility is critical to improving formulations using both current chemistry and new chemistry. Key dimensions of improvement are increasing test data points and improving inferencing abilities for a given body of test data. The graph 400 is plotted on an axis of a "test volume and formulation variations" 402 and an "ability to make confident inferences from test results" 404. The series of optimization drawings 406–412 are associated with different points along increased visibility of the formation landscape graph 400. They illustrate that it is only at a point of global optimization shown in drawing 412 that it can be ascertained that the point of current optimization, of points along the increased visibility of the formulation landscape 400 displayed by drawings 406, 408 and 410, is not the best result.

Figure 5:
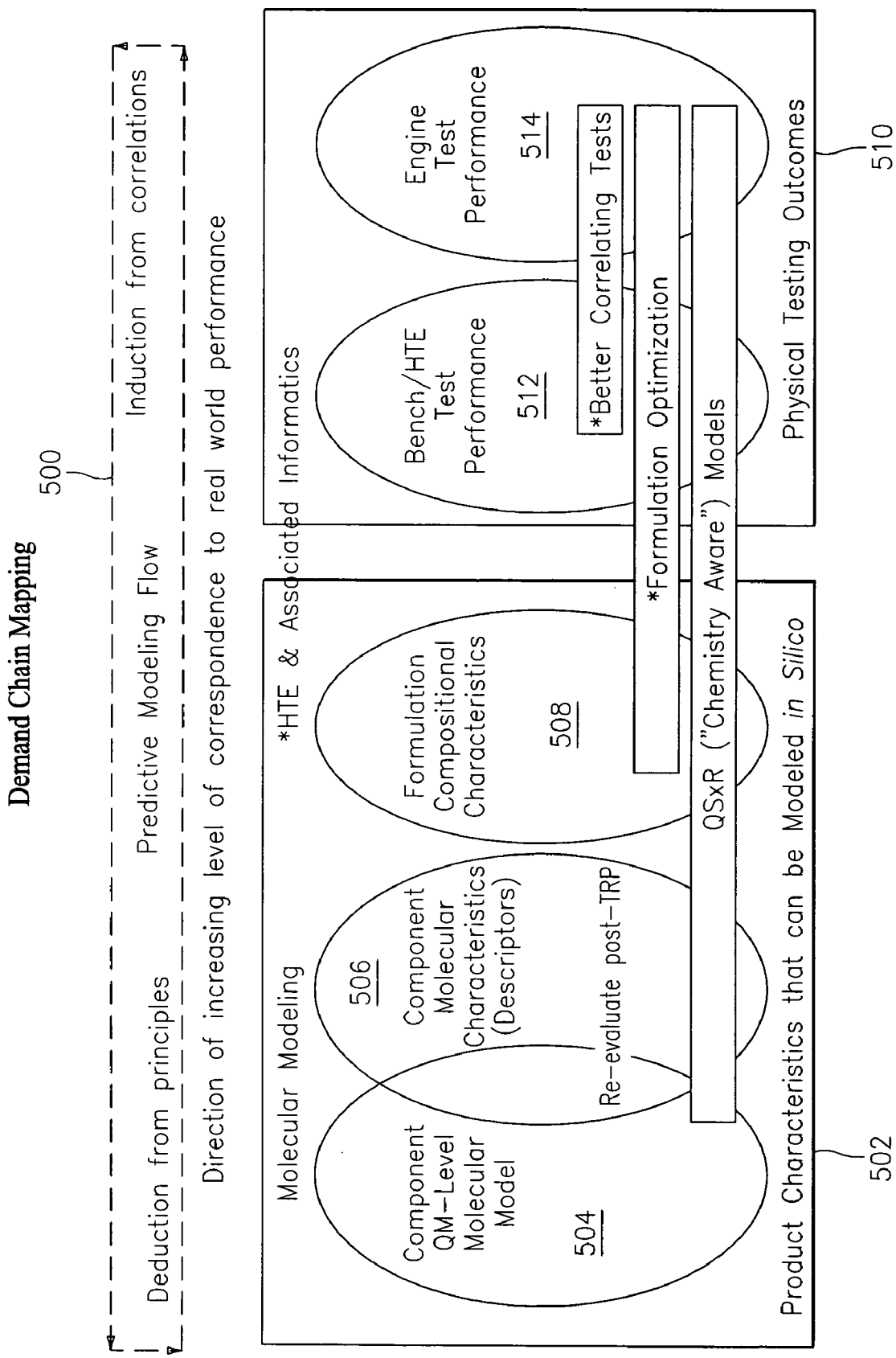

FIG. 5 illustrates the inventive product development process flow 500 from conception of an idea for a lubricant. The process 500 steps include at least:
- a computational work (in Silico) portion 502 comprising:
- quantum mechanical (QM) molecular modeling of an idea step 504;
- developing descriptors for what is important to test the QM model 506;
- formulating compositions having specific characteristics 508; and
- a physical portion 510 comprising:
- bench testing or high throughput experimentation (HTE); and
- actual engine performance.

The overall process 502 and 510 has feedback based on results and looping back 500 when things don't work as evidenced by results of the HTE and engine performance. Improving predictability of performance results at reasonable costs requires continuous improvement across in Silico modeling and physical testing processes.

Molecular Modeling

During the component QM-Level molecular modeling 504, a hypothesis exists about the possible mechanism of how a reaction mechanistically operates. For example, a tester working on a new anti-oxidant may hypothesize how peroxides form in an operating internal combustion engine and further how such peroxides are subsequently destroyed before they can do damage to a lubricating oil. To support such hypothesis the tester proposes a chemical mechanism by which such chemical process occurs. The proposed chemical mechanism is in Silico tested using methods that may be embodied in computer programs for simulating technologies. Such methods relate molecular and solid state properties to the interactions of electrons. One method from Accelrys Inc., a wholly owned subsidiary of Pharmacopeia Inc, works by approximating a solution to the Schrodinger equation.

The Accelrys Inc.'s QM methods predict electronic and molecular structure and energetics. Because they are based on the fundamental equation of quantum chemistry, QM methods are much more accurate than approximations such as atomistic simulation. Vibrational modes and excited states can be predicted, enabling analysis of spectral properties. The ability to predict electronic structure enables QM to study transition states and molecular orbitals—both critical to the understanding of reaction chemistry.

By iterative studies with this software the tester thus derives a plausible mechanism for the peroxide decomposition. This involves first principle calculations of, for example, transition states, bond lengths, bond angles, etc. This, for example, gives the tester a more detailed understanding of the chemical mechanism by which peroxide destruction, and therefore protection of the oil from oxidation, occurs. With such improved knowledge the tester is thereby better able to conceive of new molecules for synthesis that will improvements over the currently available antioxidants.

Deriving Descriptors

The tester is now describing descriptors for molecules that will help him build a better antioxidant. As more and more descriptors are developed the tester is building up a Quantitative Structure Activity Relationship (QSAR) library of relevant factors that are important in predicting effective from less effective antioxidants. A QSAR library or model is a multivariant mathematical relationship between a set of physicochemical properties (descriptors) and a property of the system being studied, such as the chemical reactivity, solubility, or mechanical behavior.

An example of such a program is Accelrys Inc.'s "$C^2$·QSAR+" software. That and similar programs facilitate the graphical analysis of QSAR models to assist in the tester's perception of subtle chemical relationships in fields as diverse as drug discovery, polymers, and materials science. These programs integrate a wide range of regression and analysis technologies. Existing experimental data and simulation results can be used to predict the activities or properties of novel compounds thereby enabling prioritization of synthetic programs.

Formulation of Compositions Having Specific Characteristics

The tester must now synthesize sufficient numbers of molecules to validate his or her original hypothesis and test these molecules in a range of formulations to determine their actual properties. Chemists and robotics may each be used to help to create these molecules.

Bench Testing or (HTE);

The testing is done over a wide range of possible formulations with the HTE platform. It is necessary to study these components over a range of formulations because individual lubricating oil additives may interact with each other to either enhance or reduce their predicted activity.

At any step of this process the tester might need to loop back and restart the process of deriving descriptors 506 or all the way to the re-start the QM-Level molecular modeling. Eventually, the tester will collect a massive amount of data from the HTE. This data is then used to build a library of information on components in formulations. The library is quite extensive, as it comprises each component in combination with numerous other components and the entire mixture in multiple base oils. In particular, the library provides separate results for each formulation versus individual bench tests. The management of the data can be achieved by a high-throughput software using a relational database like Oracle or Sybase. An example of such software is the "CombiMat" program from Accelrys Inc., described on http://www.accelrys.com/mstudio/ms_matinformatics/combimat.html.

From the standpoint of cost, there is usually a preference for software solutions versus hardware solutions. It is typically less expensive to simulate with software than to develop and operate hardware solutions. However, these economics must be balanced by relative efficacy of the approaches. Therefore, everything else being equal, there would be a preference to employ:

1. Molecular modeling that predicts component and product performance from, "first principles". This element includes software only.

2. Comprehensive statistical inferencing that can correlate performance across a chain of tests, e.g., basic lab tests, bench tests, and engine tests, with the structural characteristics of the molecules of the product. A general approach to this inferencing is called Quantitative Structure-Activity Relationship (QSAR) modeling. This element includes software only.

3. High Throughput Experimentation (HTE) approaches, which enables vastly more physical tests on components and products than through conventional means. This test, includes hardware with associated informatics software.

Actual Engine Performance

Advanced statistical correlations of bench test data versus actual engine test data can now be performed. This is achieved through software like the Formulation Assisting Software Toolkit from Accelrys Inc. described at http://www.accelrys.com/mstudio/ms_matinformatics/fast.html. Such software is a workflow solution for design of formulated products that streamlines the data, information, and knowledge flow that is necessary to successfully formulate products. It is likely that no single bench test will correlate perfectly with the engine test so linear or higher order regressions of multiple wear and oxidation tests will be used to produce a weighted combination that best correlates with the engine test results. Such regression analysis is used to make predictions about a single value. Linear or higher order regression involves discovering the equation for a line or curve that best fits the given data. Such equation is then used to predict engine test results for additional formulations.

This then allows the tester to optimize the final formulation for cost/performance. That is the performance is moved in a direction that is predicted to still pass the performance but at the lowest possible cost.

As another example, the QM computations drive the in Silico modeling process that provides insight into the mechanism of problems. For example, if one wishes to prepare better antioxidants it may be important to understand the mechanism by which antioxidants function. In studying the mechanism by which certain transition metal function as a peroxide inhibitor, a quantum mechanical study of the transition states for decomposition of such peroxides may be done evaluated in Silico.

As the mechanism is further understood, so are the molecular descriptors that are useful for chemists to make, e.g., improved antioxidants. These molecular descriptors are then utilized in the QSAR software. As one further understands the QM, a larger set of descriptors is built up for helping to predict a family of chemical structures that will further improve oxidation performance. At this point the work is still performed at a computational or an in Silico level.

It may be found, for example, that one antioxidant does not function as well alone as it does in combination with other antioxidants. Further, it may be possible to regenerate certain antioxidants thereby creating a catalytic cycle and thus more efficiently utilize the combination of antioxidants compared to either one separately. By this in Silico method it becomes possible to construct, a new formulation for meeting specific performance criteria. Throughout this process new chemicals are being developed which test preconceived models and provide a feedback loop to validate prior QM models and thereby further improve the QSAR descriptors.

With a sufficient base of knowledge it becomes beneficial to run HTE to validate such in Silico created models using bench testing. To analyze this data, it becomes useful to have advanced statistical and informatics software so trends and correlations of data to performance can be evaluated. As more testing data is understood the feedback continues to the QM and QSAR, so that both become improved as real data validates or refutes earlier theories.

Finally, with high volume and improvements in bench test results one moves to the engine test performance correlation.

While the invention has been shown and described with reference to certain preferred embodiments thereof, it will be understood by those skilled in the art that various changes in form and details may be made therein without departing from the spirit and scope of the invention as defined by the appended claims.

What is claimed is:

1. A method of transforming a product development process to reduce time in bringing a product to market, the method comprising the steps of:
    (a) modeling in Silico a plurality of component molecular models;
    (b) deriving in Silico molecular characteristics (descriptors) for each of said plurality of compiled molecular models;
    (c) formulating a plurality of compositions according to compositional characteristics;
    (d) bench testing the compositions; and
    (e) correlating the compositions to actual engine performance.

2. The method of claim 1, wherein said step (a) is performed via quantum mechanical (QM) approach.

3. The method of claim 1, wherein said step (b) is performed by building up a quantitative Structure Activity relationship (QSAR) library.

4. The method of claim 1, wherein in step(c) said plurality of compositions is first formulated in Silico and then physically.

5. The method of claim 1, wherein said step(c) further comprising:
    creating at least one combinatorial library database record for each of said compositions, said at least one record having a plurality of fields for storing information about compositional characteristics.

6. The method of claim 5, wherein said information includes:
    a type and amount of at least one base oil of lubricating viscosity,
    a type and amount of at least one lubricating oil additive,
    a lubricating viscosity;
    a lubricating oil additive percentage, and
    storage stability of said compositions.

7. The method of claim 5, further comprising receiving specification requirements for a lubricating oil composition.

8. The method of claim 7, further comprising:
- selecting from a database entries corresponding to compositions having specifications comparable to the received specification requirements;
- formulating a new lubricating oil composition to comply with received specification requirements;
- testing said new lubricating oil composition for compliance with received specification requirements; and
- repeating said selecting, formulating, and testing steps until compliance with received specification requirements is achieved.

9. The method of claim 1, further comprising comparing the outcome of every step and repeating a previous step if said outcome does not comply with said received specification requirements for a lubricating oil composition.

10. A method of transforming a product development process to reduce time in bringing a product to market through high throughput experimentation and advanced statistics and informatics, to transform the product development to a level of higher correlation with engine tests and to develop better commercial products, the method comprising the steps of:
- modeling in Silico a plurality of component molecular models;
- deriving in Silico molecular characteristics (descriptors) for each of said plurality of component molecular models;
- creating at least one combinatorial library database record for each of said models, said at least one record having a plurality of fields for storing information about compositional characteristics;
- receiving specification requirements for a lubricating oil composition;
- selecting from a database entries corresponding to compositions having specifications comparable to the received specification requirements;
- formulating a new lubricating oil composition to comply with received specification requirements;
- testing said new lubricating oil composition for compliance with received specification requirements;
- repeating said selecting, formulating, and testing steps until compliance with received specification requirements is achieved; and
- correlating the lubricating oil composition to actual engine performance.

11. A system of transforming a product development process to reduce time in bringing a product to market through high throughput experimentation and advanced statistics and informatics, to transform the product development to a level of higher correlation with engine tests and to develop better commercial products, the system comprising:
- modeling means for in Silico modeling a plurality of component molecular models;
- deriving means for in Silico deriving molecular characteristics (descriptors) for each of said plurality of component molecular models;
- creating means for creating at least one combinatorial library database record for each of said models, said at least one record having a plurality of fields for storing information about compositional characteristics;
- receiving means for receiving specification requirements for a lubricating oil composition;
- selecting means for selecting from a database entries corresponding to compositions having specifications comparable to the received specification requirements;
- formulating means for formulating a new lubricating oil composition to comply with received specification requirements;
- testing means for testing said new lubricating oil composition for compliance with received specification requirements; and,
- correlating means for correlating the lubricating oil composition to actual engine performance.

* * * * *